US007666445B2

(12) United States Patent
Siegel et al.

(10) Patent No.: US 7,666,445 B2
(45) Date of Patent: Feb. 23, 2010

(54) POLYMER-BASED SURGICALLY IMPLANTABLE HALOPERIDOL DELIVERY SYSTEMS AND METHODS FOR THEIR PRODUCTION AND USE

(75) Inventors: Steven J. Siegel, Berwyn, PA (US);
Karen I. Winey, Philadelphia, PA (US);
Raquel E. Gur, Philadelphia, PA (US);
Robert H. Lenox, Califon, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 23 days.

(21) Appl. No.: 10/046,504

(22) Filed: Oct. 19, 2001

(65) Prior Publication Data

US 2002/0179096 A1    Dec. 5, 2002

Related U.S. Application Data

(60) Provisional application No. 60/242,304, filed on Oct. 20, 2000.

(51) Int. Cl.
*A61F 2/00*    (2006.01)
(52) U.S. Cl. ................................................. 424/426
(58) Field of Classification Search ................ 424/426, 424/422, 423
See application file for complete search history.

(56) References Cited

U.S. PATENT DOCUMENTS

| 4,450,150 | A | * | 5/1984 | Sidman ........................ 424/424 |
| 4,883,666 | A |   | 11/1989 | Sabel et al. .................. 424/422 |
| 5,047,536 | A | * | 9/1991 | Nichols ........................ 546/61 |
| 5,490,962 | A | * | 2/1996 | Cima et al. .................. 264/401 |
| 5,601,835 | A |   | 2/1997 | Sabel et al. .................. 424/424 |
| 5,629,008 | A |   | 5/1997 | Lee ............................ 424/426 |
| 5,648,096 | A | * | 7/1997 | Gander et al. ................ 424/489 |
| 5,665,428 | A |   | 9/1997 | Cha et al. .................... 427/213.3 |
| 5,817,343 | A |   | 10/1998 | Burke ......................... 424/489 |
| 5,871,778 | A |   | 2/1999 | Kino et al. ................... 424/489 |
| 5,989,463 | A |   | 11/1999 | Tracy et al. .................. 264/4.1 |
| 6,004,573 | A |   | 12/1999 | Rathi et al. .................. 424/426 |
| 6,117,949 | A |   | 9/2000 | Rathi et al. .................. 525/415 |
| 6,130,200 | A | * | 10/2000 | Brodbeck et al. ............. 514/2 |
| 6,143,314 | A |   | 11/2000 | Chandrashekar ............. 424/426 |
| 6,147,072 | A | * | 11/2000 | Bymaster et al. ............. 514/220 |
| 6,166,173 | A | * | 12/2000 | Mao et al. .................... 528/398 |
| 6,201,072 | B1 |   | 3/2001 | Rathi et al. .................. 525/415 |
| 6,303,137 | B1 | * | 10/2001 | Dittgen et al. ............... 424/426 |
| 2002/0179096 | A1 |   | 12/2002 | Siegel et al. |

FOREIGN PATENT DOCUMENTS

EP    669128   B1  *   1/2000

WO    WO 94/10982   *   5/1994

OTHER PUBLICATIONS

Cheng et al. "A poly(D, L-lactide-co-glycolide) microsphere depot system for delivery for haloperidol," J. Controlled Release, 1988, pp. 203-212.*
Cheng et al. (J. Controlled Release, 1988, 203-212).*
Cheng et al., "A poly(D,L-lactide-co-glycolide) microsphere depot system for delivery of haloperidol," in Journal of Controlled Release 55 (1998) 203-212.*
Domb et al. "(Degradable Polymers for Site-Specific Drug Delivery," in polymers for Advanced Technologies, vol. 3, pp. 279-292, 1992.*
Benelli et al., "Clonazepam microencapsulation in poly-D, L-lactide-co-glycolide microspheres", J. Microencapsulation 1998 15(4):431-443.
Cheng et al., "A poly (D,L-lactide-co-glycolide) microsphere depot system for delivery of haloperidol", J. Controlled Release 1988 203-212.
Cheng et al., "Schizophrenia and Drug Delivery Systems", J. Drug Targeting 2000 8(2):107-117.
Fischel-Ghodsian et al., "Analysis of Drug Release Kinetics from Degradable Polymeric Devices", J. Drug Targeting 1993 1:51-57.
Heller J., "Controlled release of biologically active compounds from bioerodible polymers" 1979.
Holland et al., "Polymers for Biodegradable Medical Devices. 1. The Potential of Polyesters as Controlled Macromolecular Release Systems", J. Controlled Release 1986 4:155-180.
Jain et al., "Controlled delivery of drugs from a novel injectable in situ formed biodegradable PLGA microsphere system", J. Microencapsulation 2000 17(3):343-362.
Kitchell et al., "[32] Poly(lactic/glycolic acid) Biodegradable Drug-Polymer Matrix Systems", Polymer Systems 1985 436-449.
Köhler et al., "A new animal model of dopamine supersensitivity using s.c. implantation of haloperidol releasing polymers", Neuroscience Letters 1994 99-102.
Kulkarni et al., "Biodegradable Poly(lactic acid) Polymers", J. Biomed. Mater. Res. 1971 5:169-181.
Lewis D.H., "Controlled Release of Bioactive Agents from Lactide/Glycolide Polymers", Biodegradable Polymers as Drug Delivery Systems.
Linhardt R. J., "Biodegradable Polymers for Controlled Release of Drugs", Biodegradable Polymers 53-83.
Natsugoe et al., "Controlled Release of Cisplatin Incorporated into Biodegradable Poly-d, 1-Lactic Acid", Anticancer Research 1997 17:1957-1960.
Ron et al., "Erodible Systems", 199-217.

(Continued)

*Primary Examiner*—Blessing M Fubara
(74) *Attorney, Agent, or Firm*—Mark S. Cohen; Pearl Cohen Zedek Latzer, LLP

(57) ABSTRACT

Surgically implantable drug delivery systems for long-term delivery of haloperidol containing a biodegradable polymer and haloperidol fabricated into the surgically implantable drug delivery systems via solvent casting and compression molding are provided. Also provided are methods for producing the surgically implantable drug delivery systems and methods for using these systems in the treatment of psychotic disorders such as schizophrenia.

2 Claims, No Drawings

OTHER PUBLICATIONS

Roskos et al., "Degradable Controlled Release Systems Useful for Protein Delivery", Degradable Controlled Release Systems Chapter 2 1997 45-92.

Wada et al., "In Vitro Evaluation of Sustained Drug Release from Biodegradable Elastomer", Pharmaceutical Research 1991 8(10):1292-1296.

Wang et al., "Synthesis, characterization, bodegradation, and drug delivery application of biodegradable lactic/glycolic acid polymers: I. Synthesis and characterization", J. Biomater. Sci. Polymer Edn. 2000 11(3):301-318.

Domb et al "Degradable Polymers for Site-specific Drug Delivery" Polymers for Advanced Technologies, vol. 3, pp. 279-292, 1992.

Santos et al "Clinical implications of determination of plasma haloperidol levels" Acta Psychiatr Scand 1989: 79:348-254.

* cited by examiner

POLYMER-BASED SURGICALLY IMPLANTABLE HALOPERIDOL DELIVERY SYSTEMS AND METHODS FOR THEIR PRODUCTION AND USE

INTRODUCTION

This application claims the benefit of priority from U.S. Provisional Patent Application Ser. No. 60/242,304, filed Oct. 20, 2000.

FIELD OF THE INVENTION

The invention relates to surgically implantable drug delivery systems for the long-term delivery of antipsychotic drugs, and in particular haloperidol. The surgically implantable drug delivery systems of the present invention comprise a biodegradable polymer, preferably a lactide-co-glycolide copolymer, and an antipsychotic drug, preferably haloperidol, fabricated into an implant via solvent casting and compression molding. As demonstrated herein, these formulations, when implanted underneath the skin, release an effective amount of the antipsychotic drug over a period of months. Also provided in the present invention are methods for producing and using these surgically implantable drug delivery systems in the treatment of patients with psychotic disorders such as schizophrenia.

BACKGROUND OF THE INVENTION

While much research regarding the treatment of schizophrenia has focused on new pharmaceutical compounds, a major correctable cause for treatment resistance remains nonadherence with prescribed medication (Fenton et al. Schizophr. Bull. 1997 23(4):637-51; Kane, J. J. Clin. Psychopharmacol. 1985 5(3 Suppl):22s-27s). Approximately 50% of patients with schizophrenia and other chronic psychotic conditions are believed to be poorly adherent with prescribed medication (Young et al. Bull. Am. Acad. Psychiatry Law 1986 14(2):105-22). A controlled study to measure adherence with a detectable marker reported that 80% of patients with schizophrenia do not take medications as prescribed (Kapur et al. Schizophr. Res. 1991 6(1):49-53). Studies of relapsed patients have reported only 30% to meet the criteria for good adherence in the months prior to admission (Bergen et al. Aust. N Z J. Psychiatry 1998 32(6):815-22; Razali et al. Acta Psychiatr. Scand. 1995 91(5):331-5).

Therapeutic failure secondary to nonadherence often results in deterioration in social function and more intensive interventions including rehospitalization, such that nonadherence was the most important predictor of rehospitalization in a state hospital population (Casper, E. S. and Regan, J. R. Can. J. Psychiatry 1993 38(10):657-61). Furthermore, length of stay upon rehospitalization is shorter among medication adherent patients and they are less likely to require involuntary admission (McEvoy et al. J. Nerv. Ment. Dis. 1984 172 (7):412-6). Without antipsychotic treatment, 75% of patients with schizophrenia relapse within one year of first presentation, compared to 15% of treated patients (Ayuso-Gutierrez, J. L and del Rio Vega, J. M. Schizophr. Res. 1997 28(2-3): 199-206; Davis, J. M. and Andriukaitis, S. J. Clin. Psychopharmacol. 1986 6(1 Suppl):2S-10S). Discontinuation of antipsychotic medication also has been disclosed to increase risk of relapse approximately 5-fold (Robinson et al. Arch. Gen. Psychiatry 1999 56(3):241-7). Similarly, a study that followed first episode patients for 2 years found relapse rates up to 90% for non-medicated patients (Ram et al. Schizophr. Bull. 1992 18:185-207). Furthermore, good adherence following discharge from the hospital can reduce recidivism from 73% to 27% within one year (Gaebel, W. and Pietzeker, A. Pharmacopsychiatry 1985 18(3):235-9).

Consequences of medication nonadherence can extend beyond the health of the patient. While the majority of people with schizophrenia do not engage in violent behavior, a subset of patients display aggression during periods of psychosis (Casper, E. S. and Regan, J. R. Can. J. Psychiatry 1993 38(10):657-61; Lindqvist, P. and Allebeck, P. Br. J. Psychiatry 1990 157:345-50; Mitchell, E. W. Med. Sci. Law 1999 39(1):23-30; Tam et al. Psychiatr. Serv. 1996 47(1):86-8).

Efforts to increase medication adherence have incorporated behavioral and psychoeducational programs, family interventions and intensive supportive services (Agarwal et al. Int. J. Soc. Psychiatry 1998 44(2):92-106; Amador, X. F. and Gorman, J. M. Psychiatric. Clin. North Am. 1998 21(1): 27-42; Bustillo et al. Harv. Rev. Psychiatry 1999 6(5):229-40; Yong et al. Bull Am. Acad. Psychiatry Law 1986 14(2):105-22).

Pharmacological approaches to improved adherence include improving tolerability and efficacy of antipsychotic medication (Bustillo et al. Harv. Rev. Psychiatry 1999 6(5): 229-40; Kane, J. Br. J. Psychiatry Suppl. 1999 37:26-9; Kasper, S. Int. Clin. Psychopharmacol. 1998 13 Suppl 3:S71-7; Mauskopf et al. J. Clin. Psychiatry 1999 60(Suppl 19):14-9) through development of new agents and administration of monthly depot preparations of existing agents.

Decreased rates of discontinuation were reported for a newer agent, olanzapine, than an older one (haloperidol) (Tran et al. J. Clin. Psychiatry 1997 Jun 58(5):205-11; Tran et al. J. Clin. Psychiatry 1997 Jun 58(6):275). However, newer agents have been reported to have additional side effects including weight gain, sedation, drooling, Q-T prolongation and agranulocytosis (Campbell et al. Br. J. Clin. Pharmacol. 1999 47(1):13-22; Wetterling, T. and Mussigbrodt, H. E. J. Clin. Psychopharmacol. 1999 19(4):316-21).

Monthly depot preparations have been reported as an effective means to decrease relapse and rehospitalization (Gerlach, J. Int. Clin. Psychopharmacol. 1995 9 Suppl 5:17-20). Treatment for noncompliant patients with depot formulations (Haldol-decanoate) is much less expensive per year than oral preparations of newer neuroleptics (risperidone; Galzer, W. M. and Ereshefsky, L. J. Clin. Psychiatry 1996 57(8):337-45). However, a 7-year study of depot medication found a significant number of patients fail to comply with monthly injections and discontinuation linked to relapse (Curson et al. Br. J. of Psychiatry 1985 146:469-74). Therefore, while depot medication improves adherence initially, many patients still become nonadherent (Weiden et al. Psychiatric Services 1995 46(10):1049-54).

In contrast, a surgically implantable preparation can last for many months, providing patients with symptomatic improvement and possibly delayed disease progression for periods of time never before possible. Additionally, in the event of unacceptable side effects, implants can be removed. This offers a degree of reversibility not presently available with depot formulations. Further, surgically implantable formulations can be employed as a safety net in combination with oral dosing to achieve adjustments as clinically indicated.

Surgically implantable drug delivery systems have been applied in contraception, drug addiction, chemotherapy and pain management. The most widely used, NORPLANT®, (Wyeth Laboratories Inc. Philadelphia, Pa.) provides 5 years of contraception using levonorgestrel in silicon tubing, allowing for steady state diffusion of active ingredient (Woutersz, T. B. Inter. J. of Fertility 1991 3(51):51-6). Silicon-based delivery systems are ideal for hormonal delivery due to picogram daily dose requirements. However, this range is not suited for antipsychotics due to slow rates of release.

Polymer based delivery systems release milligram range daily dosing required for antipsychotic medications. The polymers used in these systems were initially used in surgical applications (Kulkarni et al. Arch. Surg. 1966 93(5):839-43), but have been modified to integrate medications to form surgically implantable or injectable formulations that release drug over weeks to months. These materials are divided into two categories, namely non-erodible and bioerodible polymers.

Non-erodible polymers release drug primarily by diffusion while leaving the delivery matrix in place. Non-erodible ethylene vinyl acetate (EVA) is a widely used non-erodible material. Subcutaneous delivery of haloperidol has been demonstrated in rats up to 250 days using EVA (Kohler et al. Neuroscience Letter 1994 170(1):99-102). This preparation delivered steady state levels of haloperidol in vitro with physiologic effects on striatal dopamine receptor regulation.

Bioerodible polymers release medication by erosion of the polymer matrix and diffusion of drug through the remaining polymer matrix. Examples of bioerodible polymers include, but are not limited to, high molecular weight polymers of lactic and glycolic acids, which can be used individually or in lactide-co-glycolide copolymers (PLGA). Advantages of PLGA copolymers include low antigenicity and clearance of breakdown products (lactic and glycolic acid) through the Krebs cycle. These materials have been used in microspheres for injectable depot preparations of chlorpromazine (Gao et al. J. Microencapsul. 1998 15(1):75-83) and haloperidol (Cheng et al. J. Controlled Release 1998 55(2-3):203-12) and are now in clinical use with risperidone alkermes with the extension .com/index_news.html of the world wide web, Apr. 22, 1999). Microspheres are delivered as a suspension, and last approximately 2 weeks.

Various drug delivery devices comprising biodegradable polymers are disclosed generally in, for example, U.S. Pat. No. 5,665,428, U.S. Pat. No. 5,817,343, U.S. Pat. No. 5,871,778, U.S. Pat. No. 5,989,463, U.S. Pat. No. 6,004,573, U.S. Pat. No. 6,117,949, U.S. Pat. No. 6,143,314, and U.S. Pat. No. 6,201,072. These patents each contain an extensive list of possible active agents or therapeutic classes of drugs which are suggested to be deliverable via the drug delivery device.

In addition, U.S. Pat. No. 4,883,666 teaches encapsulation of a compound for treatment of ischemic, metabolic, congenital or degenerative disorders of the central or peripheral nervous system within an implantable biocompatible polymeric device. At col. 13, lines 51-59, it is taught that polymer implants with antipsychotics can be used to treat schizophrenia. Polymer implants used in the examples of the '666 patent all comprised the non-erodible polymer ethylene vinyl acetate (EVA) and dopamine. Further, coating of the implant with a layer of EVA except for one or two holes was required for linear release. Use of bioerodible polymers in implants is suggested at col. 7, line 60 of this patent. However, no examples of implants comprising bioerodible polymers and specific therapeutic agents are taught.

U.S. Pat. No. 5,601,835 teaches similar formulations to those taught in U.S. Pat. No. 4,883,666. However, these formulations are implanted directly into the central nervous system. Again, no examples of implants comprising bioerodible polymers and specific therapeutic agents are taught.

As shown herein, however, not all pharmaceutical agents, and more particularly antipsychotic agents, are amenable to delivery via systems comprising bioerodible polymers.

SUMMARY OF THE INVENTION

An object of the present invention is to provide a surgically implantable drug delivery system comprising a biodegradable polymer, preferably a lactide-co-glycolide copolymer, and an antipsychotic drug, preferably haloperidol, fabricated into an implant via solvent casting and compression molding.

Another object of the present invention is to provide a method of producing surgically implantable drug delivery systems for haloperidol which comprises dissolving the haloperidol and a biodegradable polymer, preferably a lactide-co-glycolide copolymer, in an organic solvent; solvent casting the haloperidol and biodegradable polymer solution; and molding under compression the solvent cast solution into a surgical implant.

Another object of the present invention is to provide a method for treating patients with psychotic conditions and diseases which comprises surgically implanting into a patient suffering from a psychotic condition or disease a surgically implantable drug delivery system comprising a biodegradable polymer, preferably a lactide-co-glycolide copolymer, and an antipsychotic drug, preferably haloperidol, which have been fabricated into an implant via solvent casting and compression molding.

DETAILED DESCRIPTION OF THE INVENTION

The present invention relates to a surgically implantable preparation of an antipsychotic agent such as haloperidol which provides superior treatment outcomes due to improved medication adherence. The surgically implantable preparations of the present invention are designed to last for months to years, providing for symptomatic improvement as well as possibly delaying disease progression for periods of time never before possible. Advantages of administration of antipsychotic drugs via the surgically implantable delivery systems of the present invention include lower dosing and steady state serum drug levels, with fewer resultant side effects. Increased bioavailability with less variation in absorption and no first pass metabolism also decrease variation in plasma levels between individuals for a given dose. These factors promote antipsychotic efficacy with reduced drug exposure and side effects. Additionally, the surgically implantable drug delivery systems of the present invention can be used as a low-dose safety net for relapse prevention, with variable oral dosing of typical or atypical agents for maximum treatment benefit and supplementation during exacerbations. Finally, in the event of unacceptable side effects, such as neuroleptic malignant syndrome, the implant can be removed, thus offering a degree of reversibility not available with depot formulations.

Surgically implantable delivery systems for haloperidol have now been created using biodegradable polymers. In a preferred embodiment, the polymer comprises polylactide or a copolymer comprising polylactide such as a lactide-co-glycolide copolymer. Preferred biodegradable polymers comprise about 50 to 100% polylactide and 0 to 50% polyglycolide. The copolymer and antipsychotic drug, haloperidol, are fabricated into an implant via solvent casting and compression molding. In a preferred embodiment of this method, the individual polymers and haloperidol are dissolved in an organic solvent and solvent cast at a temperature at which the solvent evaporates for a period of time which allows for complete drying of the polymer-drug mixture. For example, for haloperidol and polymers dissolved in acetone, it has been found that solvent casting at a temperature of about 60° C. for approximately 72 hours evaporates all the solvent and results in a completely dry haloperidol-polymer mixture. Complete drying can be assessed by weighing the material at the beginning of solvent casting and at the end of the solvent casting to ensure that all solvent has been evaporated. Haloperidol concentrations preferably range from about 20% to about 40% in the delivery system depending upon the release period. Inclusion of haloperidol in the drug delivery system actually increases the stability of the drug delivery system. Thus, the higher the concentration of haloperidol, the more extended the period of release. This increase in stability does not occur with all drugs. In fact, other antipsychotic drugs such as thiothixene decreased stability and the period of release of the drug delivery system when drug concentrations were increased. Solvent cast material is then compression molded at a temperature and pressure which allows the polymer-drug material to flow into the mold. For example, compression molding at 80° C. and 25,000 psi (density 1.1±0.05 grams/cc) has been demonstrated to be suitable for haloperidol implants of the present invention.

Implants of the present invention were characterized in vitro for release kinetics. Implants comprising 75:25 PLGA with 40% haloperidol resulted in a pattern of release characterized by an initial phase of slow release (mean=0.04 mg/day for an average of 21 mg haloperidol load per implant) from 0 to 28 days. This rate corresponds to approximately 0.21%/day during the first month. A second phase of more rapid release occurred between 28 and 84 days (0.27 mg/day per implant), corresponding to approximately 1.29%/day. Implants comprising 85:15 PLGA with 40% haloperidol displayed a similar pattern of release with a phase of slow release (mean=0.05 mg/day for an average of 21 mg haloperidol load per implant) from 0 to 56 days, corresponding to approximately 0.24%/day during the first 2 months. A second phase of more rapid release occurred between 56 and 140 days (0.23 mg/day per implant), corresponding to approximately 1.1%/day. Release from a theoretical composite system of 75:25 and 85:15 PLGA, 40% haloperidol, shows an early phase from 0 to 28 days with an average of 0.14 mg/day and more rapid release between 28 to 140 days with 0.37 mg/day. Since these values result from an average drug load of approximately 42 mg, the percent released is 0.33%/day during days 0-28 and 0.88%/day during days 28-140. The value for the positive control solution (100 ng/ml) remained stable throughout the period of 140 days. Based on these release rates, a 4 month supply of haloperidol can be delivered via a 500 mg implant of the present invention comprising 40% haloperidol.

Implants of the present invention were also evaluated in vivo in rodents for bioactivity. These measures included behavioral testing with apomorphine stimulated locomotion in mice, and western blot analyses of D2 receptor expression following implantation in rats. For these experiments, implant compositions were developed to create a staged series of implants that release drug for 5 months. Animals treated with haloperidol implants displayed increased striatal D2 receptor expression as well as increased apomorphine stimulated locomotion.

In behavioral testing with apomorphine stimulated locomotion, mice were tested 3 weeks after receiving implants made of 75:25 PLGA alone or 75:25 PLGA with 20% haloperidol. Baseline locomotor activity was measured for twenty minutes. Animals with control implants traveled a mean of 12223±433 cm, while those with haloperidol containing implants traveled an average of 7664±450 cm. Thus, mice with haloperidol implants traveled significantly less distance that the controls ($p<0.001$). Implants were then removed and all animals were allowed to recover for 48 hours. After recovery, animals received apomorphine 0.5 mg/kg i.p. twenty minutes prior to locomotor testing, which has been shown to increase locomotor activity in mice (Ninan, I. and Kulkarni, S. K. Psychopharmacology (Berl) 1999 142(2):175-81). After apomorphine challenge, animals that had control implants traveled a mean of 4721±476 cm, while those with haloperidol containing implants traveled a mean of 8531±2536 cm. Therefore, following removal of implants and exposure to apomorphine, mice that had haloperidol implants traveled more distance than control mice ($p<0.02$).

A mean serum level of 26 ng/ml was measured in mice implanted with haloperidol-PLGA pellets one month following implantation.

Western blots of striatal membranes from all rats revealed a band at an apparent molecular weight of approximately 50 kD corresponding to the predicted molecular weight of the full-length D2 receptor protein (Expert Protein Analysis System, Swiss Institute of Bioinformatics, expasy with the extension .ch of the world wide web; Bunzow et al. Nature 1988 336(6201):783-7). Mean optical density of bands were quantified relative to the corresponding band for haloperidol-treated rats. Results based on three blots yielded a mean±SD relative to density for haloperidol implant-treated rats of 0.90±0.07 for the 50 kD band. The mean±SD relative density for control rats was 0.64±0.02 ($p=0.0002$, one tail t-test). An additional band of 25 kD was also labeled, likely corresponding to the intracellular portion of the D2 receptor containing the antigenic peptide against which the antibody was raised. Quantification of the 25 kD band yielded a relative density of 0.88±0.12 for haloperidol treated animals and 0.66±0.14 for control animals ($p=0.04$, one tail t-test).

Implants of the present invention have also been placed in monkeys. Monkeys with implants exhibited motor side effects consistent with haloperidol release within one day of implantation. Haloperidol serum levels in the monkeys were assessed at baseline and days 5, 12, 19, 27, 40 and 55 following implantation. Data are depicted in the following Table.

| Time (days) | Number of Monkeys | Mean | SD |
|---|---|---|---|
| baseline | 3 | 0.00 | 0.00 |
| 5 | 3 | 6.91 | 0.38 |
| 12 | 3 | 5.36 | 1.32 |
| 19 | 3 | 5.30 | 0.48 |
| 27 | 2 | 9.27 | 6.16 |
| 40 | 2 | 21.05 | 8.49 |
| 55 | 2 | 16.71 | 1.74 |

Interestingly, not all pharmaceutical agents nor all antipsychotic agents are amendable to this delivery system. For example, incorporation of the antipsychotic agent thiothixene into the implant requires lowering of the molding temperature by 40° C. and causes an acceleration in degradation of the polymer as opposed to an extension of degradation time as observed with haloperidol. Further, implant comprising thiothixene degraded at room temperature without exposure to an aqueous environment within 6 months. These implants discolored to a yellow shade and liquefied. In contrast, haloperidol implants of the present invention are stable in storage for periods exceeding one year without any signs of discoloration or change in consistency. Incorporation of the anti-depressant Fluoxetine into this delivery system resulted in an implant which caused tissue necrosis in 8 out of 8 mice tested. No tissue necrosis was observed in mice with control, Navane loaded or haloperidol-loaded implants.

Thus, the surgically implantable delivery system of the present invention provides a unique means for the long term delivery of haloperidol.

The delivery systems of the present invention are useful in the treatment of psychotic disorders, particularly disorders such as schizophrenia where patients are oftentimes noncompliant with their medication. The delivery system of the present invention can be surgically implanted into a patient, most preferably under the skin of the patient between the muscle and the dermis, in accordance with well known techniques. Haloperidol released from the bioerodible implant of the present invention maintains its bioactivity and is delivered at steady state concentrations to the patients for periods of five months or more. Implants of the present invention can be used alone or combined with oral supplementation of haloperidol or another antipsychotic drugs for dynamic response to optimum medication levels. Should the patient exhibit unwanted side effects to the haloperidol, the implant can be easily removed.

The following nonlimiting examples are provided to further illustrate the present invention.

EXAMPLES

Example 1

Implant Fabrication

Implants were fabricated through solvent casting and compression molding. Two polymers, 75% polylactide with 25% polyglycolide (75:25 PLGA) and 85% polylactide with 15% polyglycolide (85:15 PLGA) are present in a combined system of release during a 5-month period. Each copolymer has a distinctive period of degradation, which is determined by the ratio of lactide to glycolide and the molecular weight of the resulting molecule produced. An additional polymer of 100% polylactide (PLA) was used for in vivo testing in rats. All polymers (Alkermes Inc., Cincinnati, Ohio), has an inherent viscosity of 0.66-0.8 DL/gram in chloroform and a molecular weight distribution between 120-140 kD. Individual polymers and haloperidol (Sigma, St. Louis, Mo.) were dissolved in acetone and solvent case at 60° C. for 72 hours. Solvent cast material was compression molded at 80° C. and 25,000 psi (density 1.1±0.05 grams/cc).

Example 2

In Vitro Assay

Individual implants were placed in 1 liter of phosphate buffered saline (PBS), pH 7.0 at 37° C. in constant motion. Haloperidol amount was measured by GCMS (National Medical Services, Willow Grove, Pa.). Each assay included negative controls of implants made of polymer alone and a 100 ng/ml haloperidol standard to assess stability of haloperidol in solution over time.

Example 3

Animals

Implants were tested in rats (Harlan, Indianapolis, Ind.) (n=9) and mice (Jackson Labs, Bar Harbor, N. Mex.) (n=16). All animals were housed in an AAALAC accredited animal facility at the University of Pennsylvania. Institutional Animal Care and Use Committee (IACUC) approved all protocols. Animals were maintained with a 12:12 light:dark cycle with all testing and procedures performed during the light cycle.

Example 4

Implantation/Removal Surgery

Mice and rats were anesthetized with ketamine/xylazine (100/10 mg/kg, i.p.). A 1-cm incision was made in the skin on the dorsal aspect of the animal and an implant was placed between dermis and muscle. Removal of implants was performed with identical anesthesia and incision followed by implant retrieval.

Example 5

Behavioral Testing

Bioactivity of haloperidol implants was assessed in mice and rats. Sixteen C57bl/6 mice received implants made of 75:25 PLGA alone (n=8) or 75:25 with 20% haloperidol (n=8) to assess the effects of implants on locomotion. Following three weeks of implantation, total distance traversed was assessed over a twenty-minute period. Implants were then removed and animals allowed to recover for 48 hours prior to retesting 20 minutes after apomorphine challenge (0.5 mg/kg i.p.) (Sigma, St Louis, Mo.).

Example 6

Western Blot

Six Sprague Dawley rats received implants made of PLA with 30-40% haloperidol. Three rats received implants of PLA alone. Implants remained in all animals for three months prior to removal. Seventy-two hours after implant removal, rats were sacrificed and brains rapidly removed, dissected into four regions (cortex, hippocampus, striatum and cerebellum) then frozen in liquid nitrogen. Western blots for quantitative analysis of D2 receptor protein were performed on striatum. Three concentrations of cortex protein from a single animal (2.5, 5 and 10 µg) were run with all blots as an internal control to insure intensity of labeling was within linearity of quantitative software. Only those blots in which the density of samples was within the linear range of internal standards were used for analyses. Western blots were performed using polyclonal antibody, WR-3526, raised against amino acids 272-282 of the D2 receptor protein (Research and Diagnostic Antibodies, Berkeley, Calif.). Striata were homogenized in homogenization buffer (20 mM HEPES, 2 mM EGTA, 1 mM PMSF, 2 µM Aprotinin and 2 mM DTE), followed by a 30-second sonication. Samples were centrifuged 100,000 g for 1 hour at 4° C. Pellets were resuspended and solubilized in homogenization buffer containing 0.1% Triton X-100. Proteins were extracted on ice for 45 minutes with occasional agitation. After extraction, proteins were centrifuged at 30,000 g for 30 minutes at 4° C. Protein samples were prepared with 25% 4× NuPAGE sample buffer plus 10% reducing agent (Invitrogen) and heat shocked at 70° C. for 10 minutes. Samples were separated on a 10% precasted mini-gel at 200 volts for 50 minutes. Proteins were transferred to PVDF at 30 volts for 1 hour. Blots were blocked with 5% milk TBS (20 mM Tris, pH=7.5, 0.5 mM NaCl), then washed for 15 minutes. Blots were then incubated overnight with anti-D2-receptor antibody, washed with TBS, and incubated with goat-anti-rabbit horseradish peroxidase conjugate (BioRad, 1:4800) for 1 hour. Blots were then incubated with chemiluminescent substrate (Pierce) for 1 minute, wrapped with plastic and exposed to autoradiographic film.

Example 7

Quantification

The intensity of each band was quantified using a densitometer model 7100 and quantitative analysis software (Bio Rad, Hercules, Calif.) and expressed as a ratio to the corresponding band in rat 1 to yield a ratio of intensity (rat 1=ratio of 1). All samples were processed simultaneously on a single blot to allow for quantitative comparisons between conditions.

What is claimed is:

1. A method of producing an individual, surgically implantable implant which is surgically implanted underneath the skin of a patient for delivery of steady state concentrations of haloperidol to the patient for 5 months or more comprising: (a) dissolving between about 20% and 40% haloperidol and a biodegradable polymer consisting essentially of polylactide or lactide-co-glycolide copolymer in acetone; (b) solvent casting the haloperidol and biodegradable polymer solution to produce a completely dry haloperidol-polymer material; and (c) molding under compression the dry haloperidol-polymer material at a temperature and pressure which allows the haloperidol-polymer material to flow into a mold for the individual, surgically implantable implant which is surgically implanted underneath the skin of the patient, delivers steady state concentrations of haloperidol to the patient for 5 months or more, and is removable following implantation into the patient in the event the patient exhibits unwanted side effects following implantation.

2. The method of claim 1 wherein the biodegradable polymer has 50-100% polylactide and 0-50% polyglycolide.

* * * * *